United States Patent
Han et al.

(10) Patent No.: US 10,174,288 B2
(45) Date of Patent: Jan. 8, 2019

(54) INDUCED PLURIPOTENT STEM CELL MODEL FOR CARDIOFACIOCUTANEOUS SYNDROME AND USES THEREOF

(71) Applicant: Korea Advanced Institute of Science and Technology, Daejeon (KR)

(72) Inventors: Yong-Mahn Han, Daejeon (KR); Kyu-Min Han, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/103,271

(22) PCT Filed: Dec. 11, 2013

(86) PCT No.: PCT/KR2013/011484
§ 371 (c)(1),
(2) Date: Jun. 9, 2016

(87) PCT Pub. No.: WO2015/088073
PCT Pub. Date: Jun. 18, 2015

(65) Prior Publication Data
US 2016/0355788 A1    Dec. 8, 2016

(30) Foreign Application Priority Data
Dec. 11, 2013 (KR) .......................... 10-2013-0153569

(51) Int. Cl.
| | |
|---|---|
| *C12N 5/00* | (2006.01) |
| *C12N 5/02* | (2006.01) |
| *C12Q 1/68* | (2018.01) |
| *C12N 5/074* | (2010.01) |
| *G01N 33/50* | (2006.01) |
| *C12Q 1/6881* | (2018.01) |
| *C12Q 1/6883* | (2018.01) |
| *C12N 5/079* | (2010.01) |

(52) U.S. Cl.
CPC ......... *C12N 5/0696* (2013.01); *C12N 5/0618* (2013.01); *C12Q 1/6881* (2013.01); *C12Q 1/6883* (2013.01); *G01N 33/5073* (2013.01); *C12N 2503/00* (2013.01); *C12N 2506/45* (2013.01); *C12Q 2600/158* (2013.01)

(58) Field of Classification Search
CPC .................................... C12N 5/00; C12Q 1/68
See application file for complete search history.

(56) References Cited

U.S. PATENT DOCUMENTS

2011/0217774 A1    9/2011    Kim et al.

FOREIGN PATENT DOCUMENTS

| KR | 10-2012-0118619 | 10/2012 |
| KR | 10-2013-0133598 | 12/2013 |
| WO | 2011-130217 | 10/2011 |
| WO | WO 2011/130217 | * 10/2011 |

OTHER PUBLICATIONS

Koch et al A rosette-type, self-renewing human ES cell-derived neural stem cell with potential for in vitro instruction and synaptic integration PNAS_Mar. 3, 2009_vol. 106_No. 9_3225-3230.*
Han et al Enhanced SMAD1 Signaling Contributes to Impairments of Early Development in CFC-iPSCs SMAD1 Signaling in Early Development of CFCiPSCs Stem cells (Dayton, Ohio) / Stem Cells (Durham, NC, U. S.)vol. and Issue No. vol. 33 Issue: 5 pp. 1447-1455 Publication Date: May 2015.*
Chambers et al Highly efficient neural conversion of human ES and iPS cells by dual inhibition of SMAD signaling Nature Biotechnology vol. 27 No. 3 Mar. 2009 pp. 275-280.*
Carvajal-Vergara et al., Patient-specific induced pluripotent stem cell derived models of LEOPARD syndrome Nature. Jun. 10, 2010; 465(7299): 808-812.*
Lowry et al ., Generation of human induced pluripotent stem cells from dermal fibroblasts PNAS Feb. 26, 2008 vol. 105 No. 8 2883-2888.*
Carvajal-Vergara et al. (2010) "Patient-Specific Induced Pluripotent Stem-Cell-Derived Models of LEOPARD Syndrome," Nature 465:808-812.
International Search Report for PCT/KR2013/011484, dated Aug. 28, 2014.
Bentires-Alj et al., (2006) Nature Medicine, 12(3), 283-285.
Lee et. al, (2009) Journal of Genetic Medicine, 6, 87-90.

(Continued)

Primary Examiner — Maria G Leavitt
(74) Attorney, Agent, or Firm — Leydig, Voit & Mayer, Ltd.

(57) ABSTRACT

The present invention relates to an induced pluripotent stem cell (iPS) model for cardiofaciocutaneous (CFC) syndrome, a method for producing the model, and uses of the iPS model in the analysis of neural development in CFC syndrome. Specifically, the CFC syndrome-derived iPS and generation and differentiation of an embryonic body were induced from the fibroblasts of a CFC syndrome patient, and the CFC syndrome-derived iPS and embryonic body were confirmed to exhibit broken embryonic body shapes and no differentiation into neurons. When a CFC syndrome-derived embryonic body was induced by treating with p-ERK and p-SMAD1 inhibitors, the embryonic body exhibited a normal embryonic body shape and effectively differentiated into neurons. Thus, the CFC syndrome patient-derived stem cell model of the invention can be effectively used in the research for neural development in cardiofaciocutaneous syndrome.

5 Claims, 11 Drawing Sheets
Specification includes a Sequence Listing.

(56) References Cited

OTHER PUBLICATIONS

Myers et. al, (2014) Am J Med Genet A, 146(11), 2814-2821.
Robinton et. al, (2012) Nature, 481, 295-305.
Rodriguez-Viciana et al., (2006) Science, 311, 1287.
Schubbert et. al, (2007) Nature Reviews Cancer, 7(4), 295-308.
Tidyman et al., (2008) Expert reviews in molecular medicine 10: e37.

* cited by examiner

[Figure 1]
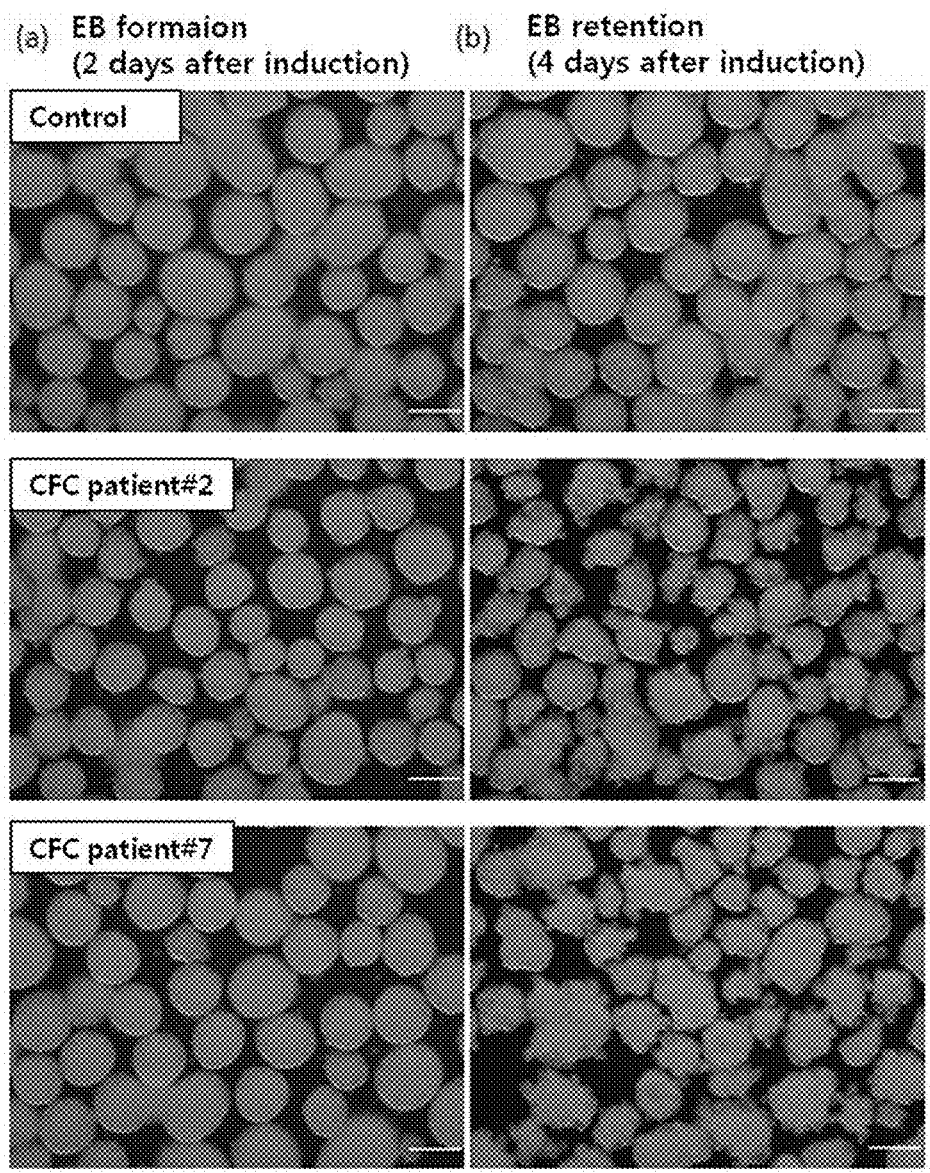

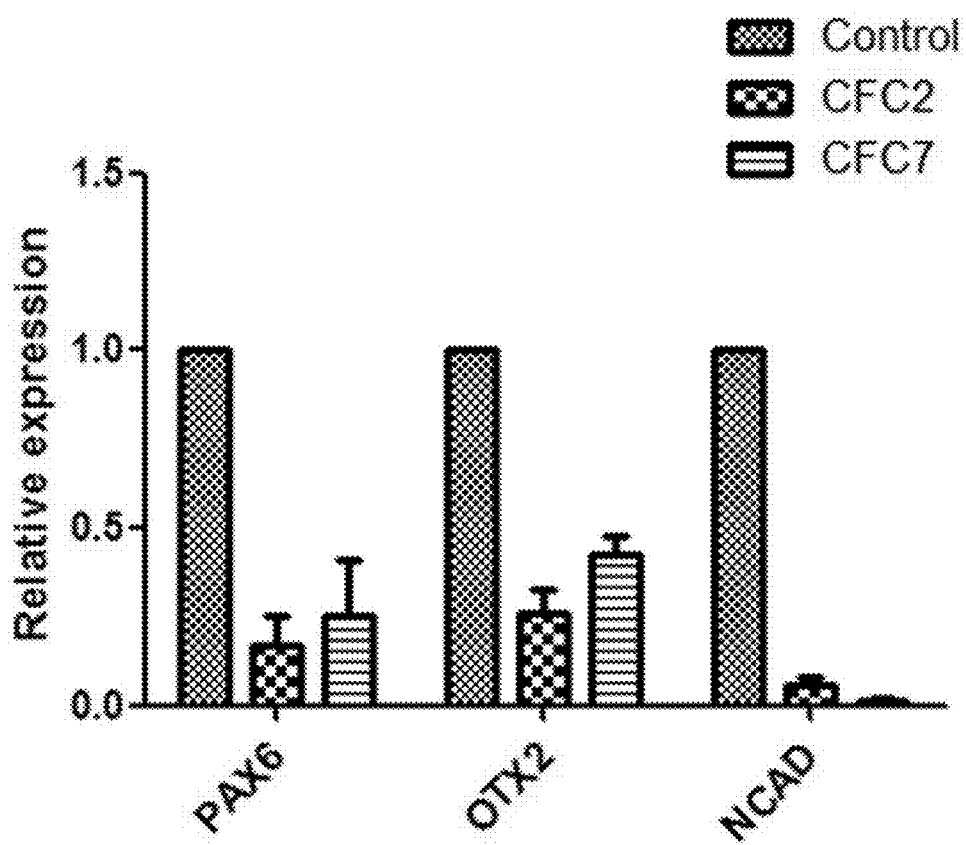
[Figure 2]

[Figure 3]
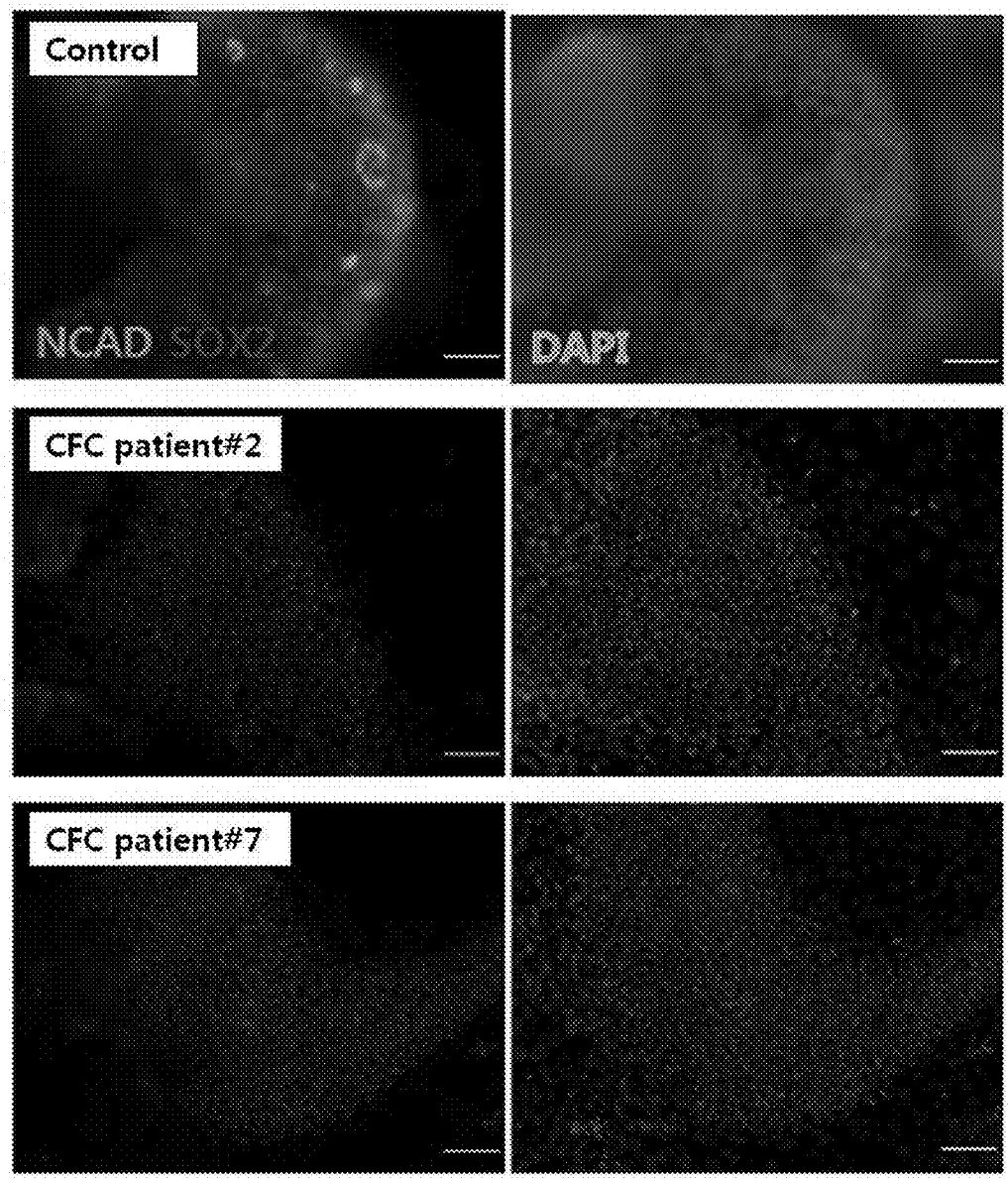

[Figure 4]
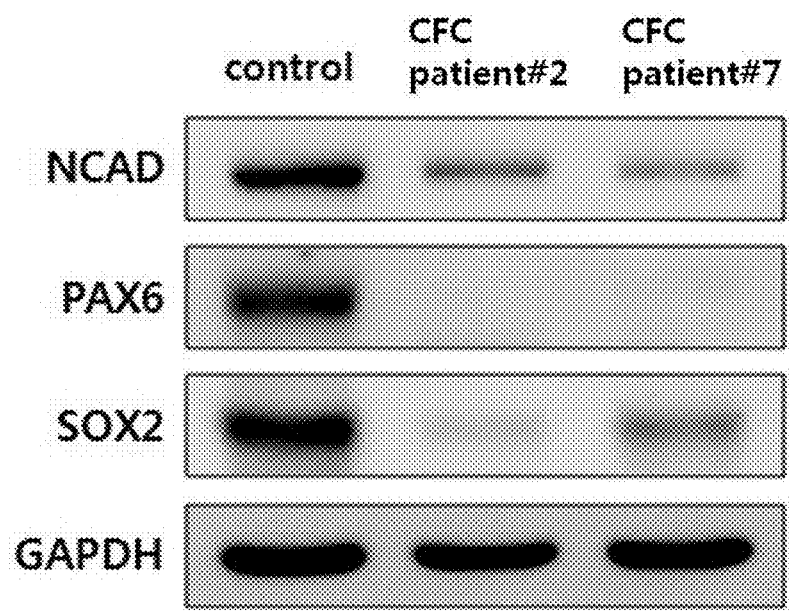

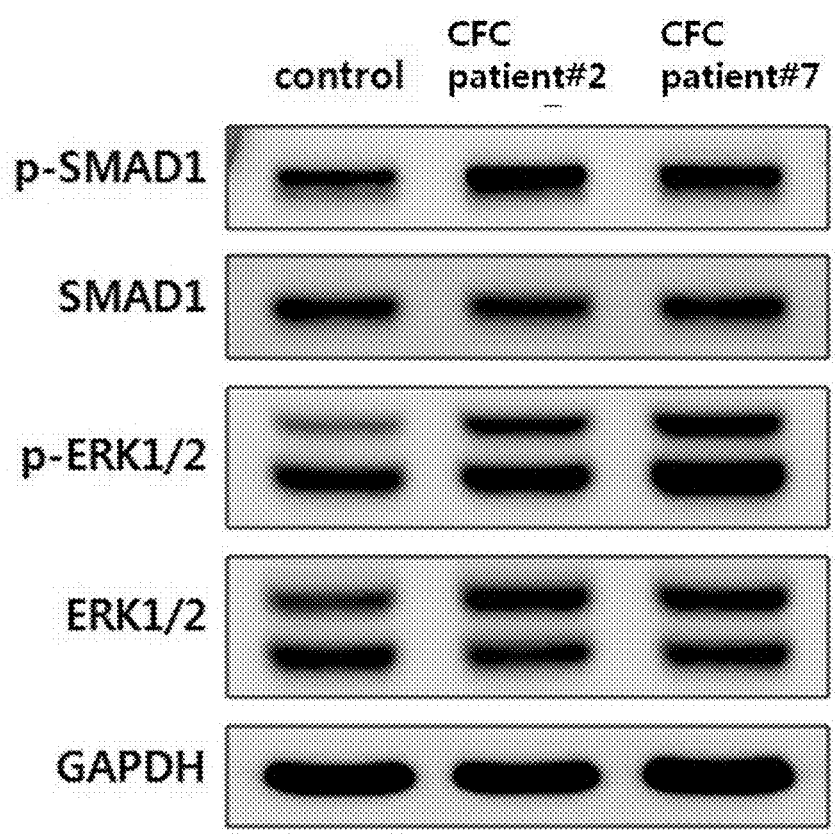
[Figure 5]

[Figure 6]
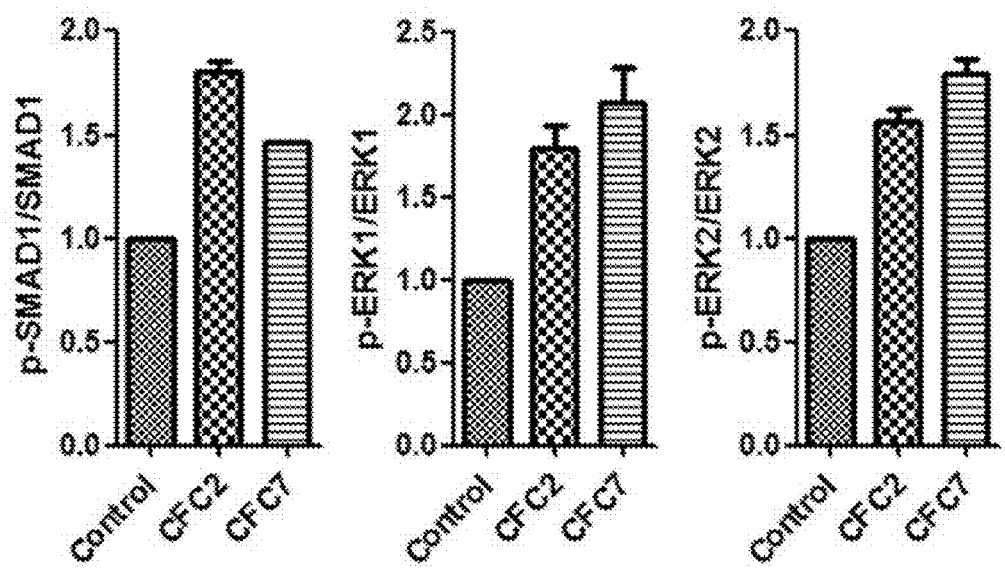

[Figure 7]
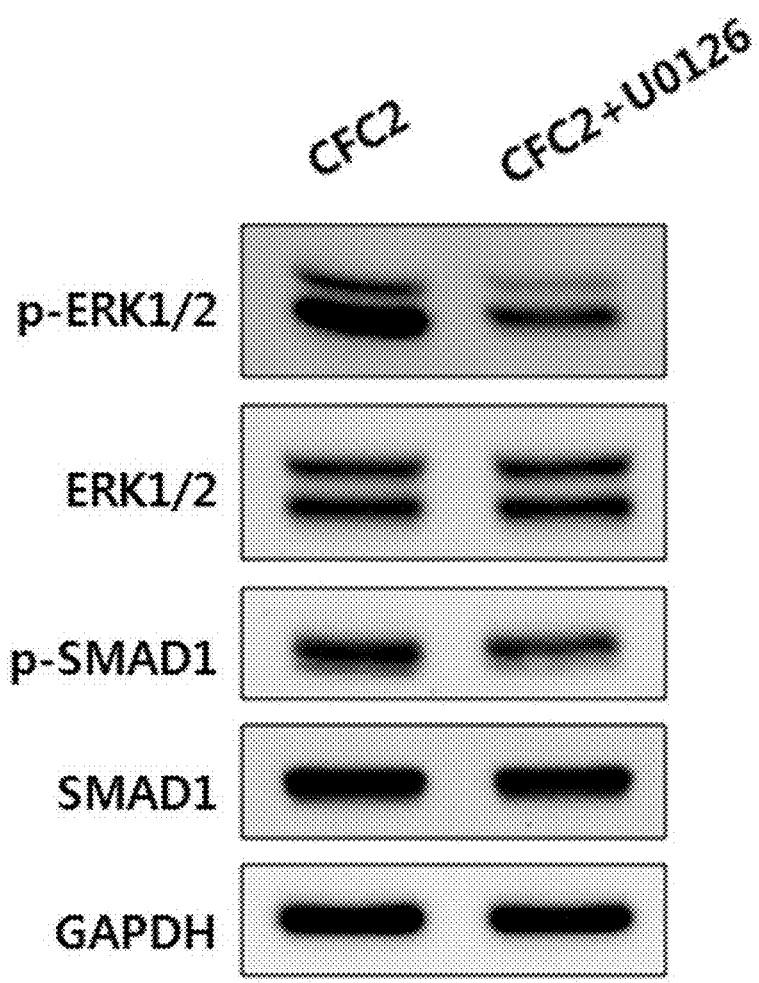

[Figure 8]
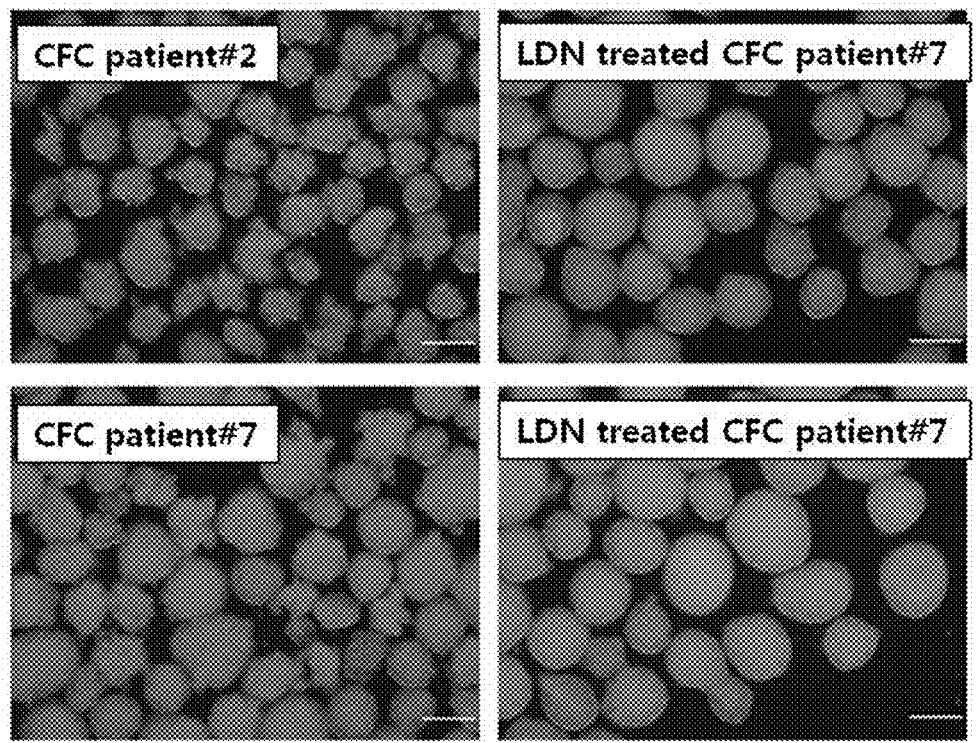

[Figure 9]
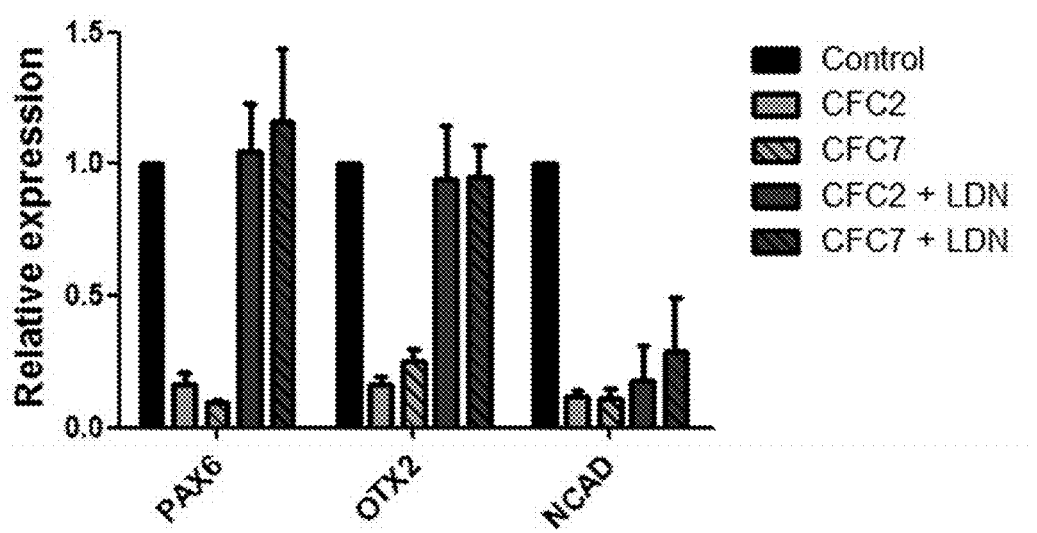

[Figure 10]
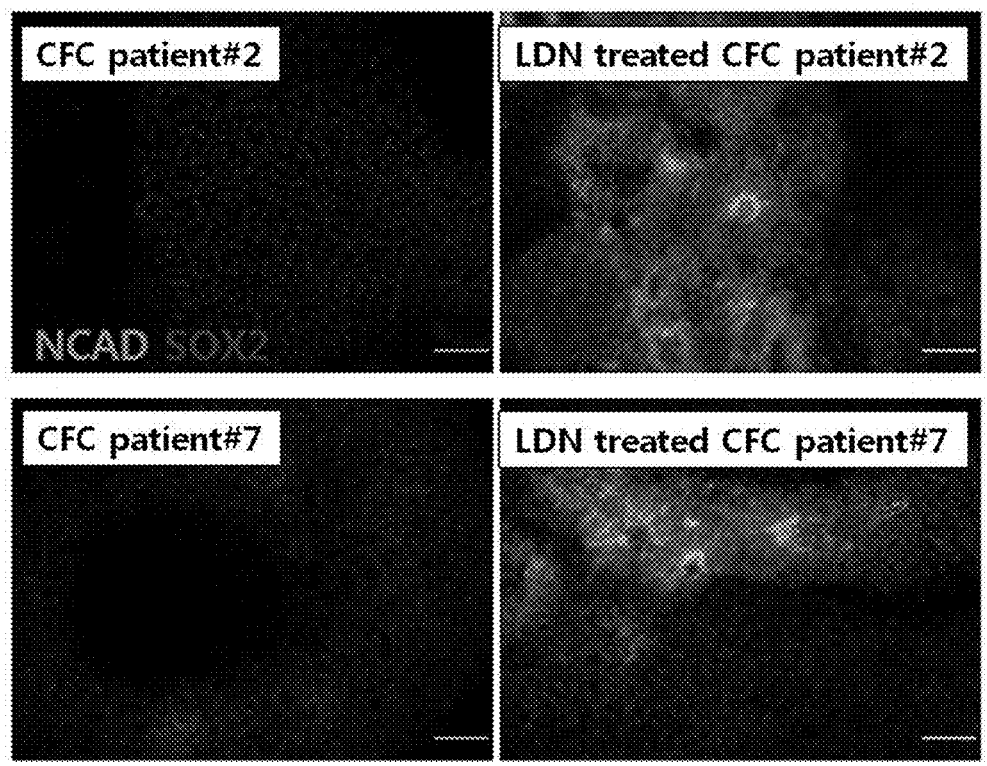

[Figure 11]
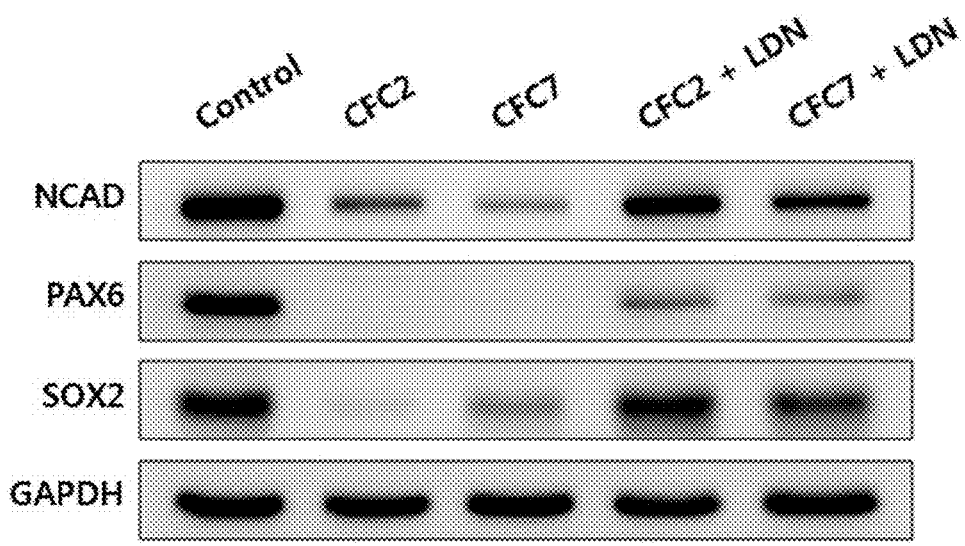

INDUCED PLURIPOTENT STEM CELL MODEL FOR CARDIOFACIOCUTANEOUS SYNDROME AND USES THEREOF

CROSS-REFERENCE TO RELATED APPLICATIONS

This application is a U.S. National Stage Application filed under 35 U.S.C. § 371of International Application No. PCT/KR2013/011484, filed Dec. 11, 2013, which claims the benefit of Korean Application No. KR 10-2013- 0153569, filed Dec. 11, 2013. Both of these applications are hereby incorporated by reference in their entireties.

BACKGROUND OF THE INVENTION

1. Field of the Invention

The present invention relates to an induced pluripotent stem cell (iPS) model for cardiofaciocutaneous (CFC) syndrome, a method for producing the model, and uses of the iPS model in the analysis of neural development in CFC syndrome.

2. Description of the Related Art

Cardiofaciocutaneous syndrome is a genetic disease accompanied by heart deformity, unique facial shape, abnormal skin condition, and retarded development. The heart deformity is exemplified by valvar pulmonary stenosis, ventricular or atrial septal defect, and hypertrophic cardiomyopathy. The unique facial shape is characterized by comparatively big head, frontal bossing, thin eyebrows, and exophthalmos. The abnormal skin is exemplified by xerosis, hyperkeratosis, ichthyosis, eczema, and loose scalp (Roberts A et al. J Med Genet (2006) 43:833-42; Armour C M and Allanson J E. J Med Genet (2008) 45:249-54). The clinical symptoms of CFC syndrome are similar to those of Noonan syndrome and thus CFC syndrome is classified into the Noonan-associated disease together with Costello syndrome and LEOPARD syndrome.

It was recently reported that RAS-MAPK (mitogen-activated protein kinase) signaling pathway associated genes including PTPN11, HRAS, KRAS, BRAF, MEK1, and MEK2 are the major cause of Noonan syndrome and Noonan-associated di seases. The mutation of those genes above causes cell growth and differentiation associated symptoms mediated by the stimulation of a growth factor. Studies on the detection and diagnosis of Noonan syndrome and Noonan-associated diseases have been focused on the screening of the gene mutation above (Jorge A A et al. Horm Res (2009) 71:185-93). However, it has not been confirmed that CFC syndrome is directly associated with the mutation of the said genes and accordingly a cause or a treatment method has not been explained, yet.

To understand Noonan syndrome and Noonan-associated syndrome, various approaches have been made. As a result, it was reported that p-ERK generated by the phosphorylation of ERK protein in the RAS-MAPK signaling pathway was up-regulated in Noonan syndrome, NF1 syndrome, and LEOPARD syndrome (T Nakamura et al. PNAS (2009), 106:36, 15436-15441; Yuan Wang et al. cell (2012) 150:4 816-830; X Carvajal-Vergara et al. Nature (2010) 465, 808-812). However, when a drug directly targeting p-ERK was used as a treating agent for Noonan syndrome and Noonan-associated syndrome, the signaling pathway was directly blocked and most likely various side effects were expected in relation to cell proliferation or cell differentiation. Therefore, it is requested to develop or to screen a drug that can indirectly inhibit p-ERK.

Stem cell is the cell in the pre-differentiation phase toward the differentiation into each cell forming different tissues, which can be obtained from each tissue of an embryo, a fetus, and an adult and characteristically exhibits self-proliferating activity enabling unlimited proliferation in undifferentiated state and pluripotency that is the potential for the differentiation into various tissues once a specific differentiation stimulus is given. Stem cell is differentiated into a specific cell by a differentiation stimulus (environment). Unlike the differentiated cell whose cell division is arrested, stem cell is self-renewal and has the ability of proliferation (expansion) and plasticity, meaning it can produce the cell that is the same as itself and at the same time it can be differentiated into different cells when the environment is changed or a different stimulus is given.

Human pluripotent stem cells including induced pluripotent stem cells (hPSCs) including induced pluripotent stem cells (iPS) have the capability of being differentiated into specific but various cell kinds. So, when induced pluripotent stem cells (iPS) are used in in vitro differentiation system, not only therapeutic potential including lowering the risk of immunorejection is increased but also the mechanism of complex disease in the early stage of organogenesis can be easily understand, making them as an efficient evaluator (Muotri, A. R. (2009) Epilepsy Behav 14 Suppl 1: 81-85; Marchetto, M. C., B. Winner, et al. (2010) Hum Mol Genet 19(R1): R71-76).

Therefore, the present inventors tried to establish a stem cell model for the research of CFC syndrome. The inventors induced the development and differentiation of CFC syndrome-derived induced pluripotent stem cells (iPS) into embryonic body from the fibroblasts of a CFC syndrome patient and then confirmed that the CFC syndrome-derived iPS and embryonic body exhibited broken embryonic body shapes and no differentiation into neurons. The inventors also induced CFC syndrome-derived embryonic body by treating with p-ERK and p-SMAD1 inhibitors. As a result, the embryonic body displayed a normal embryonic body shape and was effectively differentiated into neurons. Therefore, the method for cell modeling of CFC syndrome using the iPS of the invention can be efficiently used for the screening of CFC syndrome treating agents, leading to the completion of the invention.

SUMMARY OF THE INVENTION

It is an object of the present invention to provide novel induced pluripotent stem cells (iPS) harboring the same characteristics as cardiofaciocutaneous syndrome (CFC syndrome) patient cells and uses of the same for the screening of drug candidates for the neural development and treatment of CFC syndrome.

To achieve the above object, the present invention provides a method for preparing a CFC syndrome iPS model in vitro, comprising the following steps:

i) inducing the dedifferentiation of the fibroblasts separated from a cardiofaciocutaneous syndrome (CFC syndrome) patient into induced pluripotent stem cells (iPS) in vitro; and ii) collecting the iPS induced in step i).

The present invention also provides a CFC syndrome iPS model prepared by the method of the invention above.

The present invention further provides a method of using the iPS as a CFC syndrome model, comprising the following steps:

i) inducing the differentiation of an embryonic body (EB) or neurons from the iPS above; and ii) analyzing the expression of a differentiation marker in the embryonic body or neurons induced in step i).

The present invention also provides a method for screening CFC syndrome treating agent candidates, comprising the following steps:

i) treating the test compound or the composition to the said iPS model or the embryonic body or neurons induced from the iPS model;

ii) analyzing the characteristics of the iPS model, embryonic body, or neurons of step i); and iii) comparing the results analyzed in step ii) with the non-treated control.

The present invention also provides a use of the CFC syndrome iPS model prepared by the method of the invention.

In addition, the present invention provides a method of using the iPS as a CFC syndrome model, comprising the following steps:

i) inducing the differentiation of an embryonic body (EB) or neurons from the iPS above; and ii) analyzing the expression of a differentiation marker in the embryonic body or neurons induced in step i).

ADVANTAGEOUS EFFECT

The stem cell model using the induced pluripotent stem cells (iPS) derived from the fibroblasts of a CFC syndrome patient is efficient in investigating the embryonic body shape and the differentiation into neurons of the same, so that it can be effectively used in the research for neural development in cardiofaciocutaneous syndrome.

BRIEF DESCRIPTION OF THE DRAWINGS

The application of the preferred embodiments of the present invention is best understood with reference to the accompanying drawings, wherein:

FIG. 1 is a diagram illustrating the shape of the embryonic body (EB) differentiated from the induced pluripotent stem cells (iPS) derived from a cardiofaciocutaneous syndrome (CFC syndrome) patient.

FIG. 2 is a diagram illustrating the relative expressions of PAX6, OTX2 and NCAD genes in CFC-iPS derived embryonic body, compared with the control.

FIG. 3 is a diagram illustrating the results of immunofluorescence performed to measure the expressions of SOX2, NCAD, and neural resette in CFC-iPSC derived neurons (CFC-neurons).

FIG. 4 is a diagram illustrating the results of Western blotting performed to measure the expressions of PAX6, SOX2, and NCAD in CFC-neurons.

FIG. 5 is a diagram illustrating the levels of p-SMAD1, p-ERK1, and p-ERK2 in CFC-embryonic body.

FIG. 6 is a diagram illustrating the comparison of the phosphorylation levels of SMAD1, ERK1, and ERK2 in CFC-embryonic body.

FIG. 7 is a diagram illustrating the downregulations of p-ERK1/2 and p-SMAD1 in the CFC embryonic body (CFC2+U0126) differentiated by the treatment of a p-ERK inhibitor.

FIG. 8 is a diagram illustrating the shape of the CFC-embryonic body (LDN treated CFC patient) differentiated by the treatment of a p-SMAD1 inhibitor.

FIG. 9 is a diagram illustrating the relative expressions of PAX6, OTX2 and NCAD in CFC2+LDN and CFC7+LDN, compared with the normal control and non-treated control (CFC2 and CFC7).

FIG. 10 is a diagram illustrating the results of immunofluorescence performed to measure the expressions of SOX2, NCAD, and neural resette in the CFC-neurons (CFC patient+LDN) differentiated by the treatment of a p-SMAD1 inhibitor.

FIG. 11 is a diagram illustrating the results of Western blotting performed to measure the expressions of PAX6, SOX2, and NCAD in the CFC-neurons differentiated by the treatment of a p-SMAD1 inhibitor.

DESCRIPTION OF THE PREFERRED EMBODIMENTS

Hereinafter, the present invention is described in detail.

The present invention provides a method for preparing a CFC syndrome iPS model in vitro, comprising the following steps:

i) inducing the fibroblasts separated from a cardiofaciocutaneous syndrome (CFC syndrome) patient into induced pluripotent stem cells (iPS) in vitro; and ii) collecting the iPS induced in step i).

The present invention also provides a CFC syndrome iPS model prepared by the method of the invention above.

The inducement in step i) above is preferably performed by using the ectopic expression of the pluripotent marker including OCT4, SOX2, KLF4, and C-MYC, but not always limited thereto.

In a preferred embodiment of the present invention, the present inventors confirmed the clinical symptoms and mutant genes in a CFC syndrome patient (see Table 1) and then induced the differentiation of iPS (CFC-iPS) from the fibroblasts of the CFC patient above.

Therefore, since the CFC syndrome iPS model of the present invention exhibits the same characteristics as CFC syndrome patient cells, the method for preparing the iPSC model of the invention can be effectively used for the study of neural development in CFC syndrome.

The present invention further provides a method of using the iPS as a CFC syndrome model, comprising the following steps:

i) inducing the differentiation of an embryonic body (EB) or neurons from the iPS above; and ii) analyzing the expression of a differentiation marker in the embryonic body or neurons induced in step i).

The said embryonic body is preferably characterized by at least one of the following characters, but not always limited thereto:

i) broken embryonic body shape; and ii) unexpression of neuroectoderm marker genes including PAX6, OTX2 and NCAD.

The said neurons are preferably characterized by at least one of the following characters, but not always limited thereto:

i) down-regulation of neuronal marker proteins including PAX6, SOX2, and NCAD; and ii) decrease of neural rosette formation.

In the method above, the inducement is preferably either spontaneous inducement or direct inducement achieved by the addition of an inducing substance, and at this time, the inducing substance is preferably a neuronal differentiation promoter including N2 or B27, but not always limited thereto. The preferable concentration of the inducing substance in the medium is preferably 5~100 ng/ml and more preferably 10~80 ng/ml, and most preferably 20 ng/ml, but not always limited thereto.

In a preferred embodiment of the present invention, the inventors induced the differentiation of an embryonic body (CFC-embryonic body) from CFC-iPS in order for the embryonic body to have pluripotency. As a result, 2 days after the inducement of the differentiation, a CFC-embryonic body was formed in the shape of sphere like a WT-embryonic body. 4 days after the inducement of the differentiation, the embryonic body was no more in the shape of sphere and became broken (see FIG. 1). In addition, the neuroectoderm genes PAX6, OTX2 and NCADHERIN were significantly down-regulated compared with the WT-embryonic body (see FIG. 2).

The present inventors also induced the differentiation of neurons from the CFC-embryonic body. As a result, CFC-neurons displayed the significantly low levels of PAX6, SOX2, and NCAD (see FIG. 4) and neural rosette was not even observed therein (see FIG. 3), suggesting that the abnormal differentiation of neuroectoderm in the early stage of iPS development caused mental retardation in CFC syndrome patients.

To increase the differentiation efficiency of neurons from CFC-iPS and embryonic body, the p-ERK inhibitors U0126 or the p-SMAD1 inhibitor LDN193189 was treated to CFC-embryonic body in the course of the differentiation. As a result, compared with the CFC-embryonic body differentiated without being treated with U0126 or LDN193189, the CFC-embryonic body differentiated in the presence of U0126 or LDN193189 displayed the decrease of p-ERK and p-SMAD1 (see FIGS. 5~7). The CFC-embryonic body differentiated in the presence of U0126 or LDN193189 displayed the normal unbroken embryonic body shape (see FIG. 8). The CFC-neurons differentiated with the treatment of LDN193189 displayed a significant up-regulation of NCAD, PAX6, and SOX2 marker genes and proteins, which was similar to the normal control level, and neural rosette was also recovered (see FIG. 10). Therefore, the CFC syndrome patient-derived iPSC model of the present invention is useful for the confirmation of the differentiation of neurons and for the observation of the broken embryonic body shape. The iPSC model, therefore, can be effectively used in the research for neural development in cardiofaciocutaneous syndrome.

The present invention also provides a method for screening CFC syndrome treating agent candidates, comprising the following steps:
i) treating the test compound or the composition to the said iPS model or the embryonic body or neurons induced from the iPS model;
ii) analyzing the characteristics of the iPS model, embryonic body, or neurons of step i); and
iii) comparing the results analyzed in step i with the non-treated control.

To understand the characteristics of the iPS model of step i), the differentiation potency of the iPS model into an embryonic body or neurons is preferably investigated, but not always limited thereto.

The characteristics of the embryonic body of step iii) is preferably one or more characteristics selected from the following a) ~ c), but not always limited thereto;
a) normal embryonic body shape;
b) expression of one or more neuroectoderm marker genes selected from the group consisting of PAX6, OTX2, and NCAD; and
c) decrease of the phosphorylation level of p-SMAD1, p-ERK1, or p-ERK2protein.

The characteristics of the neurons of step iii) is preferably one or more characteristics selected from the following a) ~ c), but not always limited thereto;

a) expression of one or more neuroectoderm marker proteins selected from the group consisting of PAX6, OTX2, and NCAD;
b) decrease of the phosphorylation level of p-SMAD1, p-ERK1, or p-ERK2protein; and
c) neural rosette formation.

The present invention also provides a method for screening CFC syndrome treating agent candidates, comprising the following steps:
i) treating the test compound or the composition to the said iPS model;
ii) inducing the differentiation of an embryonic body from the iPS model of step i);
iii) analyzing one or more characteristics selected from the followings in the embryonic body induced in step ii):
a) embryonic body shape;
b) neuroectoderm marker gene expression;
c) p-SMAD1, p-ERK1 or p-ERK2 level; and
iv) comparing the results analyzed in step iii) with the non-treated control.

The present invention also provides a method for screening CFC syndrome treating agent candidates, comprising the following steps:
i) inducing the differentiation of an embryonic body from the iPS model;
ii) treating the test compound or the composition to the embryonic body induced in step i);
iii) analyzing one or more characteristics selected from the followings in the embryonic body treated in step ii):
a) embryonic body shape;
b) neuroectoderm marker gene expression;
c) p-SMAD1, p-ERK1 or p-ERK2 level; and
iv) comparing the results analyzed in step iii) with the non-treated control.

In step iv) above, the comparison is to select a test compound or a composition that is able to recover the shape of the embryonic body from the broken shape to the normal shape, but not always limited thereto.

The said neuroectoderm marker gene is preferably PAX6, OTX2 or NCAD, but not always limited thereto. The comparison in step 4) is preferably to select a test compound or a composition that is able to increase the expression of the neuroectoderm marker gene, compared with that of the non-treated control, but not always limited thereto.

In step iv) above, the comparison is preferably to select a test compound or a composition that is able to decrease the phosphorylation level of one or more proteins selected from the group consisting of p-SMAD1, p-ERK1, and p-ERK2, compared with that of the non-treated control, and more preferably to select a test compound or a composition that is able to decrease the phosphorylation level of p-SMAD1, but not always limited thereto.

The stem cell model using the induced pluripotent stem cells derived from the fibroblasts of a CFC syndrome patient of the present invention is efficient in the confirmation of the broken embryonic body shape and the differentiation of neurons, so that the cell model can be effectively used for the screening of CFC syndrome treating agent candidates.

The present invention also provides a method for screening CFC syndrome treating agent candidates, comprising the following steps:
i) treating the test compound or the composition to the said iPS model;
ii) inducing the differentiation of neurons from the iPS model of step i);
iii) analyzing one or more characteristics selected from the below a)~c) in the neurons induced in step ii):

a) neuroectoderm marker protein expression;
b) p-SMAD1, p-ERK1 or p-ERK2 level;
c) neural rosette formation; and
iv) comparing the results analyzed in step iii) with the non-treated control.

The present invention also provides a method for screening CFC syndrome treating agent candidates, comprising the following steps:

i) inducing the differentiation of neurons from the iPS model;
ii) treating the test compound or the composition to the neurons induced in step i);
iii) analyzing one or more characteristics selected from the below a)~c) in the neurons treated in step ii):
a) neuroectoderm marker protein expression;
b) p-SMAD1, p-ERK1 or p-ERK2 level;
c) neural rosette formation; and
iv) comparing the results analyzed in step iii) with the non-treated control.

The neuroectoderm marker protein above is preferably PAX6, OTX2, or N-CADHERIN (NCAD), but not always limited thereto. The comparison in step iv) above is preferably to select a test compound or a composition that is able to increase the expression of the neuroectoderm marker protein, compared with the non-treated control, but not always limited thereto.

The comparison in step iv) above is preferably to select a test compound or a composition that is able to reduce the phosphorylation level of one or more proteins selected from the group consisting of p-SMAD1, p-ERK1, and p-ERK2, compared with the non-treated control, and more preferably to select a test compound or a composition that is able to reduce the phosphorylation level of p-SMAD1, but not always limited thereto.

The comparison in step iv) above is preferably to select a test compound or a composition that is able to increase the neuronal rosette formation, compared with the non-treated control, but not always limited thereto.

The stem cell model using the induced pluripotent stem cells derived from the fibroblasts of a CFC syndrome patient of the present invention is efficient in the confirmation of the broken embryonic body shape and the differentiation of neurons, so that the cell model can be effectively used for the screening of CFC syndrome treating agent candidates.

The present invention also provides a use of the CFC syndrome iPS model prepared by the method of the invention.

In addition, the present invention provides a method of using the iPS as a CFC syndrome model, comprising the following steps:

i) inducing the differentiation of an embryonic body (EB) or neurons from the iPS above; and
ii) analyzing the expression of a differentiation marker in the embryonic body or neurons induced in step i).

The stem cell model using the induced pluripotent stem cells derived from the fibroblasts of a CFC syndrome patient of the present invention is efficient in the confirmation of the broken embryonic body shape and the differentiation of neurons, so that the cell model can be effectively used for the screening of CFC syndrome treating agent candidates.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Confirmation of the Clinical Symptoms and the Mutations of Causing Genes of Cardiofaciocutaneous Syndrome (CFC Syndrome)

<1-1> Clinical Symptoms of CFC Syndrome Patients

To confirm the clinical symptoms of CFC syndrome patients, CFC syndrome patients were selected and the clinical symptoms thereof were investigated.

Particularly, CFC syndrome patients (C.J.Y) were connected in Asan medical center, Seoul, Korea, and the representative symptoms of CFC syndrome as shown in Table 1 were confirmed (Table 1).

TABLE 1

| Clinical symptoms of CFC syndrome | |
|---|---|
| Heart defect | ventricular septal defect (VSD) |
| Facial characteristics | hypertelorism |
| | macrocephalic |
| | webbed neck |
| | epicanthal folds |
| | low-set ear |
| Developmental disorders | mental retardation |
| | short stature |

<1-2> Mutation in the Causing gene of CFC Syndrome

To confirm the mutation in the causing gene of CFC syndrome, the inventors investigated the sequence of BRAF gene known as the RAS-MAPK and the CFC syndrome associated gene in the fibroblasts of a CFC syndrome patient.

Particularly, after approved by Institutional Review Board in the hospital, dermal tissue was obtained from the CFC patient selected in Example <1-1> who agreed to be a volunteer himself or through a legal representative by skin tissue biopsy using punch biopsy method after anesthetizing locally. Fibroblasts were separated from the dermal tissue obtained above, followed by culture in DMEM (Dulbecco's modified Eagle's medium; GIBCO, USA) supplemented with 10% FBS (fetal bovine serum; GIBCO, USA), 0.05 mg/ml ascorbic acid, 0.3 mg/ml L-glutamine (GIBCO, USA), 3.7 mg/ml sodium bicarbonate (NaHCO$_3$), and 100 U/ml penicillin (GIBCO, USA). Upon completion of the culture, 100 μl of the cell supernatant was inoculated in a tissue culture plate, which was maintained in 5% CO$_2$ condition at 37° C. for 3 hours. After adding 2 ml of culture medium thereto, cell culture was performed for 1 week to confirm the viability and proliferation of the fibroblasts. Then, genomic DNA (gDNA) was extracted from the fibroblasts obtained above. BRAF gene sequence was investigated by using the forward primer (BRAF_F; SEQ. ID. NO: 1: 5'-AAACAAGAGAGTAGATACGTCAGTTTC-3') and the reverse primer (BRAF_R; SEQ. ID. NO: 2: 5'-TGG-TAGGTAGAAAAGAGATATTTTTGG-3'). As a control, BRAF gene sequence of human skin fibroblasts (CRL-2097; American Type Culture Collection (ATCC), USA) was investigated by the same manner as described above, which was used as the wild type (WT) for the comparison of the gene sequence with that of a CFC patient.

As a result, in the CFC patient's gene, c.770A>G missense mutation was confirmed, by which Gln257Arg mutation in BRAF protein was caused.

EXAMPLE 2

Differentiation of CFC Patient-derived Induced Pluripotent Stem Cells (iPS) and Embryonic Body (EB)

<2-1> Inducement of the Development of iPS from CFC Patient

To execute the example of the present invention, the development of CFC-derived iPS (CFC-iPS) was induced from the fibroblasts of a CFC patient via ectopic expression using the pluripotent markers OCT4, SOX2, KLF4, and C-MYC (Takahashi, K et al, Cell 131(5): 861-872, 2007).

Particularly, the development of CFC-iPS was induced from the fibroblasts (CFC-fibroblast) of the CFC patient obtained in Example <2-1> by ectopic expression using OCT4, SOX2, KLF4, and C-MYC.

<2-2> Inducement of the Differentiation of an Embryonic Body from CFC-iPS

To investigate the pluripotency of CFC-iPS in vitro, the differentiation of an embryonic body (EB) from CFC-iPS was induced.

Particularly, the colony of CFC-iPS induced by the same manner as described in Example <2-1> was cut into 4 pieces by using McClain tissue chopper. The CFC-iPS fragments were distributed in the ultra-low attachment dish, followed by re-suspension in 5 ml of the embryonic body differentiation medium, which was DMED/F12 supplemented with 10% serum replacement (SR). After 4 days of suspension culture, the differentiation of a CFC-iPS-derived embryonic body (CFC-embryonic body) was induced. On day 2 and day 4 from the inducement, the CFC-embryonic body was obtained and the cell morphology was observed under phase contrast microscope. WT-iPS was cultured as the normal control by the same manner as described above, so that the differentiation of a WT-iPS-derived embryonic body (WT-embryonic body) was induced.

As a result, as shown in FIG. 1, the CFC-embryonic body displayed a sphere like body shape similarly to the WT-embryonic body 2 days after the inducement started. However, 4 days later, the body shape was broken and not sphere anymore (FIG. 1). Therefore, it was confirmed that CFC-iPS was damaged in the course of the differentiation into CFC-EB.

<2-2> Differentiation Potency of CFC-embryonic Body

To confirm the differentiation potency of CFC-embryonic body, the transcription levels of the neuroectoderm genes PAX6, OTX2, and NCADHERIN (NCAD) mRNAs in CFC-iPS were investigated.

Particularly, the differentiation of a CFC-embryonic body was induced by the same manner as described in Example <2-2>. 4 days later, a CFC-embryonic body was obtained and suspended in TRIzol (Invitrogen, USA), followed by the extraction of total RNA of the CFC-embryonic body according to the manufacturer's protocol. 1 µg of the extracted RNA was used to synthesize the first strand cDNA by using M-MLV reverse transcriptase (Enzynomics, USA). Then, real-time PCR was performed by using the primers listed in Table 2 with iCycler iQ5 real-time detection system (Bio-Rad laboratories, USA). The relative expression level of each gene PAX6, OTX2, and NCAD in CFC-EB was measured. As the control to correct the expression level, the expression level of GAPDH gene was measured by the same manner as the above. ΔCt value of each PAX6, OTX2, and NCAD was calculated by measuring the difference of Ct from GAPDH. The normal control, human skin fibroblasts were also induced to be differentiated by the same manner as described above, resulting in the wild type iPS (WT-iPS). The expression levels of PAX6, OTX2, and NCAD in the WT-EB were measured and compared with those of PAX6, OTX2, and NCAD in CFC-EB. The results were presented as the fold change calculated by mathematical formula 1 below.

TABLE 2

Primer sequences used in this invention

| Gene | Primer | Sequence | SEQ. ID. NO |
|------|--------|----------|-------------|
| PAX6 | PAX6_F | 5'-TGGGCGCAGACGGCATGTAT-3' | SEQ. ID. NO: 3 |
|      | PAX6_R | 5'-CGTAGGTTGCCCTGGCACCG-3' | SEQ. ID. NO: 4 |
| NCAD | NCAD_F | 5'-GATATGCTTCAACACGCTTT-3' | SEQ. ID. NO: 5 |
|      | NCAD_R | 5'-CCAAGATAATAAAATCGCTCCAT-3' | SEQ. ID. NO: 6 |
| OTX2 | OTX2_F | 5'-ATGCGAGAGGAGGAGGTGGCACT-3' | SEQ. ID. NO: 7 |
|      | OTX2_R | 5'-GTTGTTGCTGTTGTTGGCGG-3' | SEQ. ID. NO: 8 |

$$\text{Fold Change} = 2^{-(S\Delta Ct - C\Delta Ct)} \quad \text{[Mathematical Formula 1]}$$

SΔCt: ΔCt value of each gene in CFC-iPS; and
CΔCt: ΔCt value of each gene in WT-iPS.

As a result, as shown in FIG. 2, it was confirmed that the gene expressions of PAX6, OTX2, and NCAD in CFC-EB were significantly lower than those in the WT-EB, (FIG. 2).

EXAMPLE 3

Differentiation of CFC-derived Neurons

<3-1> Inducement of the Differentiation of Neurons from CFC-Embryonic Body

To confirm that CFC-embryonic body did not have the differentiation potency, the inventors induced the differentiation of CFC-EB into neurons and then investigated the intracellular expressions of SOX2 and N-CADHERIN (NCAD).

Particularly, the differentiation of a CFC-embryonic body was induced by the same manner as described in Example <2-2> for 4 days. The CFC-embryonic body was attached onto the matrigel™ coated dish containing the neuronal differentiation medium, which was DMED/F12 supplemented with the neuronal differentiation promoter N2 and B27, and cultured for 5 days. The CFC-embryonic body was cultured for total 9 days and then CFC-neurons differentiated from CFC-iPS were obtained. The obtained CFC-neurons were fixed with 4% formaldehyde at room temperature for 30 minutes. The cells were washed with PBS containing 0.1% Tween 20 (PBST) three times and then treated with 0.1% triton X-100 to give permeability to the cell membrane. Then, the cells were washed with PBST three times and then added with 3% bovine specific albumin, leading to the blocking at room temperature for 1 hour. The cells were treated with the primary antibodies anti-N-CADHERIN mouse antibody (Cell Signaling Technologies, USA) and anti-SOX2 rabbit antibody (BD Transduction Laboratories, USA), followed by over-night culture at 4° C. Then, the cells were washed with PBST. After washing, the cells were treated with Alexa Fluor 488 or Alexa Fluor 594 conjugated secondary antibody (Invitrogen, USA), followed by culture for 1 hour for the immunofluorescence of CFC-iPS. To compare the expression level, the nucleus was stained with 4'6-diamidino-2-phenylindole (DAPI), which was then observed under fluorescence microscope (Olympus, Japan) or LSM 510 confocal microscope (Carl Zeiss, Germany) to investigate the expressions of SOX2 and NCAD.

As a result, as shown in FIG. 3, the neural rosette wherein the expression of NCAD was surrounded by SOX2 to form a rose flower shape was observed in WT-neurons, while the expressions of SOX2 and NCAD were too significantly decreased in CFC-neurons to form the neural rosette (FIG. 3).

<3-2> Expression of Neural Marker Protein in CFC-neurons

To confirm the overall down-regulation of the neural marker protein in CFC-neurons, western blotting was performed and measured the expressions of PAX6, SOX2, and NCCAD in CFC-neurons.

Particularly, CFC-neurons were obtained by the same manner as described in Example <3-1> and re-suspended in EBC buffer (50 mM Tris-HCl pH 8.0, 300 mM NaCl and 0.5% NP40; Sigma-Aldrich, USA) containing 100 μg/ml lysome, 10 μg/ml aprotinin, and 10 μg/ml leupeptin. The re-suspended cells were lysed on the ice by sonication three to five times for a second, followed by centrifugation at 4° C., at 16,100×g, for 5 minutes. The supernatant containing the cell protein was obtained. The concentration of the protein was measured by brad-ford assay. The supernatant obtained from each cell was diluted in 60 mM Tris-HCl buffer (pH 6.8) containing 25% glycerol, 2% sodium dodecyl sulfate (SDS), 14.4 mM 8-mercaptoethanol, and 0.1% bromophenol blue, followed by heating for 2~3 minutes. To separate the protein that had the molecular weight of either up to 100 kDa or at least 100 kDa, the separation was performed on 10% and 6% SDS-PAGE gels and the separated protein was transferred onto the nitrocellulose membrane, followed by blocking with 4% skim milk or 5% bovine serum albumin (BSA). The membrane was treated with the primary antibody anti-PAX6 mouse antibody (Millipore), anti-SOX2 rabbit antibody (Cell Signaling Technologies, USA), or anti-N-CADHERIN mouse antibody (BD Transduction Laboratories, USA), followed by overnight culture at 4°C. The membrane was then washed with TBST and treated with the secondary antibody goat anti-rabbit IgG (H+L) (HRP conjugate; Thermo Scientific, USA) along with TBST containing 4% skim milk. After one hour culture, western blotting was performed.

As a result, as shown in FIG. 4, the expressions of PAX6, SOX2, and NCAD were significantly reduced in CFC-neurons, compared with wild type neurons, (FIG. 4) and mental retardation was observed in CFC syndrome patients because of the abnormal differentiation of neuroectoderm in the early stage of iPS differentiation.

EXAMPLE 4

Increase of the Differentiation Efficiency of the Differentiation of Neurons from CFC-iPS and CFC-embryonic Body <4-1> Expression of p-SMAD1 in CFC-iPS and CFC-embryonic Body To increase the differentiation efficiency of the differentiation of CFC-iPS and CFC-embryonic body into neurons, the phosphorylation levels of SMAD1 and SAMD2, which have been known to inhibit the differentiation of normal iPS and embryonic body into neurons (Stuart M Chambers et. al, Nature Biotechnology 27, 275-280 (2009)), were measured.

Particularly, the differentiated CFC-embryonic body was obtained by the same manner as described in Example <2-2>, followed by western blotting by the same manner as described in Example <3-2> to confirm the expressions of SMAD1, p-SMAD1, ERK1, p-ERK1, ERK2, and p-ERK2 in the CFC-embryonic body. For the western blotting, rabbit anti-Smad1 antibody (product no: #9743S; Cell Signaling, USA), rabbit anti-p-smad1/5 (S463/465) antibody (product no: #9511S; Cell Signaling, USA), rabbit p44/42 MAPK (ERK) antibody (product no: #9102; Cell Signaling, USA) or rabbit p-p44/42 MAPK (T202/Y204) (p-ERK) antibody (product no: #4370S; Cell Signaling, USA) was used as the primary antibody. As the secondary antibody, goat anti-rabbit IgG (H+L) secondary antibody (HRP conjugate; Thermo Scientific, USA) was used. The expression levels of SMAD1, p-SMAD1, ERK1, p-ERK1, ERK2, and p-ERK2 were quantified by using Image J, the program for the measurement of the pixel intensity, by which the band intensity turned into numerical value. The relative values of p-SMAD1/SMAD1, p-ERK1/ERK1, and p-ERK2/ERK2 were calculated and then the phosphorylation levels of SMAD1, ERK1, and ERK2 were compared with those of the normal control.

As a result, as shown in FIGS. 5 and 6, it was confirmed that the levels of p-SMAD1, p-ERK1, and p-ERK2 were increased in the CFC derived embryonic body (FIGS. 5 and 6).

<4-2> Changes in the Level of p-SMAD1 According to the Inhibition of p-ERK in the Course of the CFC-embryonic Body Differentiation To investigate whether or not the up-regulation of p-SMAD1 in the CFC-embryonic body was associated with p-ERK, the p-ERK inhibitor U0126 was added to the CFC-embryonic body in the course of the embryonic body differentiation.

Particularly, the differentiation of a CFC-embryonic body was induced by the same manner as described in Example <2-2> in DMED/F12 supplemented with 5 μM 1,4-diamino-2,3-dicyano-1,4-bis(2-aminophenylthio)butadiene (U0126), 100 nM 6-(4-(2-(piperidin-1-yl)ethoxy)phenyl)-3-(pyridin-4-yl)pyrazolo[1,5-a]pyrimidine (LDN193189), and 10% SR. Then, western blotting was performed by the same manner as described in Example <3-2> in order to confirm the expressions of SMAD1, p-SMAD1, ERK1, p-ERK1, ERK2, and p-ERK2 in the CFC-embryonic body.

As a result, as shown in FIG. 7, compared with the CFC-embryonic body differentiated without being treated with U0126 or LDN193189, the CFC-embryonic body differentiated in the presence of U0126 or LDN193189 displayed the down regulation of p-ERK and accordingly the level of p-SMAD1 was also reduced therein (FIG. 7).

EXAMPLE 5

Therapeutic Effect of the Inhibition of p-SMAD1 in CFC Syndrome Patients

<5-1> Changes in the Body Shape of CFC-embryonic Body According to the Inhibition of p-SMAD1 in the Course of the CFC-embryonic Body Differentiation To confirm the mitigating effect of the inhibition of p-ERK associated p-SMAD1 on the symptoms of CFC syndrome patients, LDN193189, the p-SMAD1 inhibitor, was added to the CFC-embryonic body in the course of the embryonic body differentiation.

Particularly, the differentiation of a CFC-embryonic body was induced by the same manner as described in Example <2-2> in DMED/F12 supplemented with 100 nM LDN193189 and 10% SR. 4 days after the inducement started, the CFC-embryonic body was obtained and observed under phase contrast microscope to investigate the embryonic body shape. As for the normal control, WT-iPS was cultured by the same manner as described above to induce the differentiation of a WT-iPS derived embryonic body (WT-embryonic body).

As a result, as shown in FIG. 8, compared with the CFC-embryonic body differentiated without being treated with LDN193189, the CFC-embryonic body differentiated in the presence of LDN193189 (LDN-CFC-embryonic body) displayed the normal unbroken embryonic body shape (FIG. 8).

<5-2> Differentiation Potency of CFC-embryonic Body According to the Inhibition of p-SMAD1

To confirm whether or not the differentiation potency of CFC-embryonic body was recovered when p-SMAD1 was inhibited, the inventors investigated the mRNA transcription levels of the neuroectoderm genes, PAX6, OTX2, and NCADHERIN, in LDN-CFC-embryonic body.

Particularly, the LDN-CFC-embryonic body was obtained by the same manner as described in Example <5-1>. Then, the relative expression levels of PAX6, OTX2, and NCAD-HERIN in the LDN-CFC-embryonic body by the same manner as described in Example <2-3>.

As a result, as shown in FIG. 9, compared with the normal control, the expression levels of PAX6, OTX2, and NCAD-HERIN in the CFC-embryonic body differentiated without being treated with LDN193189 were significantly reduced, while the expression levels of PAX6 and OTX2 were significantly increased in the LDN-CFC-embryonic body almost as higher as the levels of the normal control (FIG. 9).

<5-3> Differentiation of Neurons from CFC-embryonic Body According to the Inhibition of p-SMAD1

To confirm the differentiation of neurons from the CFC-embryonic body according to the inhibition of p-SMAD1, the inventors investigated the formation of neural rosette in the course of the differentiation of neurons from the LDN-CFC-embryonic body.

Particularly, the LDN-CFC-embryonic body was obtained by the same manner as described in Example <5-1>. The differentiation of neurons from the LDN-CFC-embryonic body was induced by the same manner as described in Example <3-1>. As a result, neurons differentiated from the LDN-CFC-embryonic body (LDN-CFC-neurons) were obtained. Then, immunofluorescence was performed by the same manner as described in Example <3-1> to confirm the expressions of SOX2 and NCAD. And western blotting was performed by the same manner as described in Example <3-2> to confirm the expressions of NCAD, PAX6, and SOX2 protein markers.

As a result, as shown in FIGS. 10 and 11, compared with the normal control, the neural rosette formation was not observed in the CFC-neurons differentiated without being treated with LDN193189. On the other hand, it was confirmed that the neural rosette formation was recovered (FIG. 10). It was also confirmed that the expressions of NCAD, PAX6, and SOX2 proteins were significantly increased almost as higher as the levels of the normal control (FIG. 11).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method of using induced pluripotent stem cells (iPSC) as a cardiofaciocutaneous syndrome (CFC syndrome) model comprising the following steps:

i) inducing dedifferentiation of fibroblasts separated from a CFC syndrome patient into induced pluripotent stem cells (iPSC) in vitro, wherein the fibroblasts comprise a BRAF gene which encodes a Gln257Arg BRAF protein mutation;

ii) dedifferentiating the iPSC into an embryonic body and analyzing characteristics of the embryonic body, wherein said characteristics comprise the following a)-c):

a) broken embryonic body shape compared with an embryonic body differentiated from iPSC derived from fibroblasts isolated from a normal patient without CFC syndrome and which do not encode a BRAF protein mutation;

b) unexpression of one or more neuroectoderm marker genes selected from the group consisting of Paired box 6 (PAX6), Orthodenticle homeobox 2 (OTX2), and Neural cadherin (NCAD) compared with the embryonic body differentiated from iPSC derived from fibroblasts isolated from a normal patient without CFC syndrome and without a BRAF protein mutation; and c) increase of phosphorylation levels of Phosphorylated Mothers against decapentaplegic homolog 1 (p-SMAD1), Phosphorylated Mothers against decapentaplegic homolog 2 (p-SMAD2), and Phosphorylated extracellular signal-regulated kinase (p-ERK), compared with the embryonic body differentiated from the iPSC derived from fibroblasts isolated from a normal patient without CFC syndrome and which do not encode the BRAF protein mutation, iii) selecting iPSC generated in step i), which produce embryonic bodies having broken embryonic shape, unexpression of the one or more neuroectoderm marker genes, and increased phosphorylation levels of p-SMAD1, p-SMAD2, and p-ERK, as CFC syndrome model cells.

2. The method of claim 1 wherein the broken embryonic body shape is a broken sphere shape.

3. A method of using induced pluripotent stem cells (iPSC) as a cardiofaciocutaneous syndrome (CFC syndrome) model comprising the following steps:

i) inducing dedifferentiation of fibroblasts separated from a CFC syndrome patient into induced pluripotent stem cells (iPSC) in vitro, dedifferentiating the iPSC into embryonic bodies, and inducing differentiation of neurons from the embryonic bodies, wherein the fibroblasts comprise a BRAF gene which encodes a Gln257Arg BRAF protein mutation;

ii) analyzing expression of neural differentiation markers of a) and b) below in the neurons differentiated in step i):

a) down-regulation of one or more neural differentiation marker proteins selected from the group consisting of PAX6, OTX2, and NCAD, compared with neurons differentiated from iPSC derived from fibroblasts isolated from a normal patient without CFC syndrome and which do not encode a BRAF protein mutation; and b) decrease of neural rosette formation compared with neurons differentiated from the iPSC derived from fibroblasts isolated from a normal patient without CFC syndrome and which do not encode a BRAF protein mutation, iii) selecting neurons which exhibit down-regulation of the one or more neural differentiation marker proteins and decrease of neural rosette formation as CFC syndrome model cells.

4. A method for screening agents potentially useful for treating cardiofaciocutaneous syndrome (CFC syndrome), comprising the following steps:

i) inducing dedifferentiation of fibroblasts separated from a CFC syndrome patient into induced pluripotent stem cells (iPSC) in vitro, and dedifferentiating the iPSC into an embryonic body, wherein the fibroblasts comprise a BRAF gene which encodes a Gln257Arg BRAF protein mutation;

ii) treating the embryonic body of step i) with a test agent capable of inhibiting p-SMAD1 iii) analyzing characteristics of the treated embryonic body of step ii), wherein said characteristics comprise a)~c) below; and iv) comparing results of step iii) with results from a non-treated control, wherein production of the characteristics of the following a)~c) in the treated embryonic body by the agent indicates that the agent is potentially a treating agent for CFC syndrome;

a) normal embryonic body shape;

b) expression of one or more neuroectoderm marker genes selected from the group consisting of PAX6, OTX2, and NCAD; and c) decrease of phosphorylation level of p-SMAD1, p-ERK1, or p-ERK2, compared with those of the non-treated control.

5. A method for screening agents potentially useful for treating cardiofaciocutaneous syndrome (CFC syndrome), comprising the following steps:

i) inducing dedifferentiation of fibroblasts separated from a CFC syndrome patient into induced pluripotent stem cells (iPSC) in vitro, dedifferentiating the iPSC into embryonic bodies, and inducing differentiation of neurons from the embryonic bodies, wherein the fibroblasts comprise a BRAF gene which encodes a Gln257Arg BRAF protein mutation;

ii) treating the neurons of step i) with a test agent capable of inhibiting p-SMAD1;

iii) analyzing characteristics of the treated neurons of step ii), wherein said characteristics comprise a) ~c) below; and iv) comparing results of step iii) with results from a non-treated control, wherein production of the characteristics of the following a)~c) in the treated neurons by the agent indicates that the agent is potentially a treating agent for CFC syndrome;

a) expression of one or more neuroectoderm marker proteins selected from the group consisting of PAX6, OTX2, and NCAD;

b) decrease of phosphorylation level of p-SMAD1, p-ERK1, or p-ERK2, compared with those of the non-treated control; and c) neural rosette formation.

* * * * *

SEQUENCE LISTING

```
<160> NUMBER OF SEQ ID NOS: 8

<210> SEQ ID NO 1
<211> LENGTH: 27
<212> TYPE: DNA
<213> ORGANISM: Artificial
<220> FEATURE:
<223> OTHER INFORMATION: primer

<400> SEQUENCE: 1
aaacaagaga gtagatacgt cagtttc                                        27

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
tggtaggtag aaaagagata tttttgg                                        27

<210> SEQ ID NO 3
<211> LENGTH: 20
<212> TYPE: DNA
<213> ORGANISM: Artificial
<220> FEATURE:
<223> OTHER INFORMATION: primer
```

```
<400> SEQUENCE: 3
tgggcgcaga cggcatgtat                                                20

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
cgtaggttgc cctggcaccg                                                20

<210> SEQ ID NO 5
<211> LENGTH: 20
<212> TYPE: DNA
<213> ORGANISM: Artificial
<220> FEATURE:
<223> OTHER INFORMATION: primer

<400> SEQUENCE: 5
gatatgcttc aacacgcttt                                                20

<210> SEQ ID NO 6
<211> LENGTH: 23
<212> TYPE: DNA
<213> ORGANISM: Artificial
<220> FEATURE:
<223> OTHER INFORMATION: primer

<400> SEQUENCE: 6
ccaagataat aaaatcgctc cat                                            23

<210> SEQ ID NO 7
<211> LENGTH: 23
<212> TYPE: DNA
<213> ORGANISM: Artificial
<220> FEATURE:
<223> OTHER INFORMATION: primer

<400> SEQUENCE: 7
atgcgagagg aggaggtggc act                                            23

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
gttgttgctg ttgttggcgg                                                20
```